United States Patent
Shroot et al.

(10) Patent No.: US 6,783,767 B2
(45) Date of Patent: Aug. 31, 2004

(54) LOW TEMPERATURE DISINFECTANT/ STERILANT FOR MEDICAL DEVICES AND TOPICAL APPLICATIONS

(75) Inventors: Braham Shroot, San Antonio, TX (US); Lawton A. Seal, Schertz, TX (US); James R. Hunt, San Antonio, TX (US); Jonathan Sterling, San Antonio, TX (US); Kathy Bolsen, San Antonio, TX (US); Penny L. Sitka, San Antonio, TX (US)

(73) Assignee: Healthpoint, Ltd., Fort Worth, TX (US)

( * ) Notice: Subject to any disclaimer, the term of this patent is extended or adjusted under 35 U.S.C. 154(b) by 0 days.

(21) Appl. No.: 10/071,051

(22) Filed: Feb. 8, 2002

(65) Prior Publication Data

US 2003/0157192 A1 Aug. 21, 2003

(Under 37 CFR 1.47)

(51) Int. Cl.[7] .............................................. A01N 25/12
(52) U.S. Cl. ...................... 424/421; 424/405; 424/406; 424/409; 424/657; 424/658; 424/659; 424/660; 514/159; 514/160; 514/163; 514/164; 514/557
(58) Field of Search .................. 514/64, 159, 163, 514/164, 557, 576, 578, 558, 529, 546, 552; 424/405, 657–660, 409, 421, 400, 401, 406

(56) References Cited

U.S. PATENT DOCUMENTS

| | | |
|---|---|---|
| 4,056,611 A | 11/1977 | Young |
| 4,259,383 A | 3/1981 | Eggensperger et al. |
| 4,411,893 A | 10/1983 | Johnson et al. |
| 4,514,384 A | 4/1985 | Gallina |
| 4,541,944 A | 9/1985 | Sanderson |
| 4,557,898 A | 12/1985 | Greene et al. |
| 4,670,252 A | 6/1987 | Sampathkumar |
| 4,900,721 A | 2/1990 | Bansemir et al. |
| 4,960,772 A | 10/1990 | Sebag et al. |
| 4,990,329 A | 2/1991 | Sampathkumar |
| 5,204,093 A | 4/1993 | Victor |
| 5,227,161 A | 7/1993 | Kessler |
| 5,302,375 A | 4/1994 | Viscio |
| 5,350,563 A | 9/1994 | Kralovic et al. |
| 5,877,137 A | 3/1999 | Zhou et al. |
| 5,958,984 A | 9/1999 | Devillez |
| 6,096,328 A | 8/2000 | Sagel et al. |
| 6,096,349 A | 8/2000 | Petri et al. |
| 6,200,551 B1 | 3/2001 | Morgan |

FOREIGN PATENT DOCUMENTS

| | | | |
|---|---|---|---|
| JP | 56061349 A | | 5/1981 |
| JP | 10-110194 | * | 4/1998 |

* cited by examiner

*Primary Examiner*—Neil S. Levy
(74) *Attorney, Agent, or Firm*—McKee, Voorhees & Sease, P.L.C.

(57) ABSTRACT

A powder composition which reacts in water to form in situ peroxycarboxylic acids at an anti-microbially effective concentration. Importantly, its utility is both for topical antimicrobial application and for effective low temperature disinfection/sterilization of instruments. It comprises the combination of a perborate, one or more novel acyl and/or aroyl donors, a buffering system which allows the pH to arise to about 9 for rapid formation of the peroxycarboxylic acids and then drop to about 7.5 for sustained stability and microbial kill. It preferably includes a surfactant facilitating antimicrobial efficacy, as well as other minors.

3 Claims, 1 Drawing Sheet

Theoretical D-values

D-value Change Over pH Range

LOW TEMPERATURE DISINFECTANT/STERILANT FOR MEDICAL DEVICES AND TOPICAL APPLICATIONS

FIELD OF THE INVENTION

An anti-microbial composition effective for use with both human and animal topical surfaces, including sterilization of tissue, skin and body cavities, and for disinfection/sterilization of medical devices/instruments, at or below 60° C., is described.

BACKGROUND OF THE INVENTION

Medical, dental and other instruments are often made of high quality stainless steel that can be cleaned and sterilized between uses for different patients by high temperature steam under pressure. This sterilization procedure is quick, reliable, odorless, non-toxic and inexpensive. In contrast to this situation, more and more devices are now made of heat-sensitive plastic, polymers, glass lenses and electronic components. These flexible, or rigid lensed devices allow relatively non-invasive diagnostic and treatment procedures within the body. The non-invasive procedures allowed by these heat-sensitive instruments are responsible for great advances in medical practice. During use, these instruments can be contaminated with potentially deadly pathogens such as the Human Immunodeficiency Virus (HIV), hepatitis viruses, and multiply antibiotic drug-resistant bacteria, including mycobacteria. For these reasons, it is imperative that these heat-sensitive devices be disinfected or sterilized prior to each use. The chemical germicides available for sterilization of heat-sensitive instruments have in the past had many problems that made their use difficult.

The antimicrobial properties of hydrogen peroxide have been known for many years. However, 6% hydrogen peroxide, efficacious at a low pH which is deleterious to many medical device materials, requires a minimum of 6 hours at room temperature to pass the standard Association of Official Analytical Chemists (AOAC) Sporicidal Test defining test for liquid chemical germicides in the United States. The antimicrobial properties of peracetic acid are also well known. Peracetic acid has a very sharp pungent odor, and is known as a tumor-promoting agent when tested on mouse skin. For these reasons, the use of peracetic acid as a chemical sterilant is limited to low concentrations used with enclosed systems.

Antimicrobial synergism between hydrogen peroxide and peracetic acid is a well established fact. Such compositions are prepared by mixing hydrogen peroxide and acetic acid to give equilibrated solutions of hydrogen peroxide, acetic acid, and peracetic acid. There is a great deal of scientific and patent literature regarding hydrogen peroxide-peracetic acid solutions for sterilization. By way of example only, Minntech Corporation of Minneapolis, Minn., has a kit or sterilization console for disinfecting with hydrogen peroxide-peracetic acid solutions (U.S. Pat. No. 5,400,818). However, this combination is limited by the same problems of pungent odor and potential toxicity as peracetic acid alone. This often means that such formulations are used at such dilute concentrations that rapid sporicidal activity is lost, or the solutions are limited to enclosed systems that contain the pungent fumes.

STERIS Corporation of Mentor, Ohio, markets a System 1 product. This uses a low concentration of peracetic acid (about 0.2%) contained within a machine, and is heated to 122° F. to achieve rapid sterilization. The relatively low peracetic acid concentration is broken down by the high temperature, limiting it to one single use cycle. The heated, enclosed, machine system utilizing a single-use sterilant charge is expensive and requires exclusive use of STERIS 20 sterilant and monitoring products.

Another cold sterilant of STERIS Corporation is described in U.S. Pat. No. 5,350,563. It uses the combination of a perborate and a mixture of a rapid acting acetyl donor and a slow acting acetyl donor. Similarly, the assignee of the present applicant has an earlier U.S. Pat. No. 6,096,348 on a quick acting chemical sterilant based upon the combination of hydrogen peroxide and dibasic carboxylic acids with a carboxylate salt buffering system. While the latter two described compositions have efficacy, they are somewhat complex and with respect to the common assignees '348 patent such may be perceived by some as incompatible with certain device materials because of the acid pH range.

As well, no one to date has developed a low temperature disinfectant/sterilant for instruments that can also be used as an effective antimicrobial for human and animal topical surfaces such as tissue, skin and body cavities. This has several advantages. First, the more universal applicability appeals to some consumers. Secondly, the system is simpler in component design than either of the above-described systems and therefore should involve less opportunity for failures. Other beneficial characteristics include fewer toxicity or environmental issues, and a potential for economical savings.

It is a primary objective of the present invention to provide a cold sterilant/disinfectant which has universal applicability in the sense that it can be used on both topical surfaces and on medical devices, such as endoscopes. The present invention provides this more universally applicable system with a less complex ingredient system, thus decreasing the risk of failure and the expense to prepare. These latter advantages assure real consumer benefits.

SUMMARY OF THE INVENTION

This invention relates to a powdered mixture, delivered as a loose powder, compressed powder or tablet, of a perborate, one or more novel acyl and/or aroyl donors (other than acetyl), a buffering system of one or more buffers, and preferably a surfactant which facilitates microbial kill efficacy. The result when mixed with water is a cold temperature effective sterilant (18° C.–60° C.) which allows the pH to rise to about 9 for rapid formation of one or more peroxycarboxylic acids (other than peracetic acid) and then drop to about 7.5±0.5 for sustained stability and microbial kill.

DETAILED DESCRIPTION OF THE PREFERRED EMBODIMENTS

Figure 1:
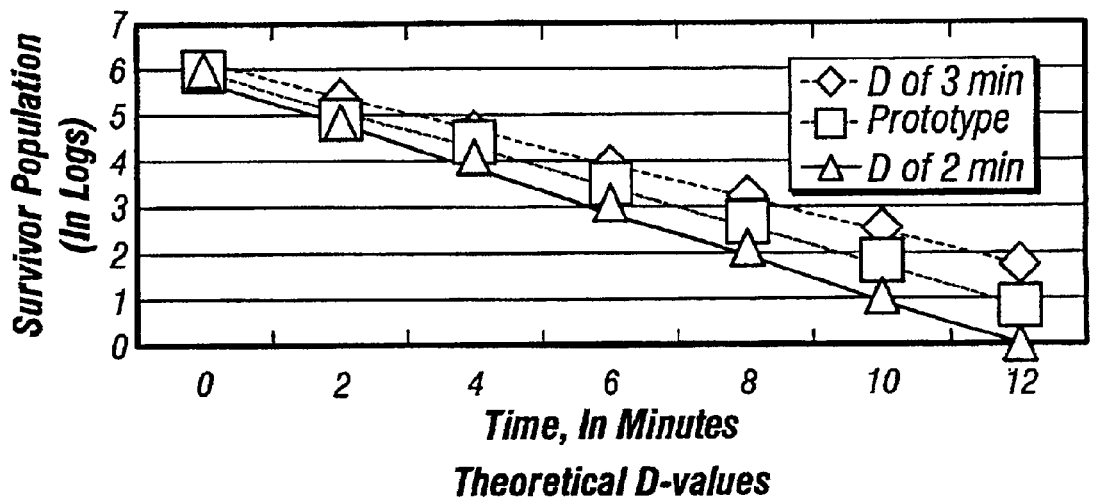
FIG. 1 shows the potential D-value (negative inverse of the slope of microbial log reduction over time) for the composition of the Example 2.
Figure 2:
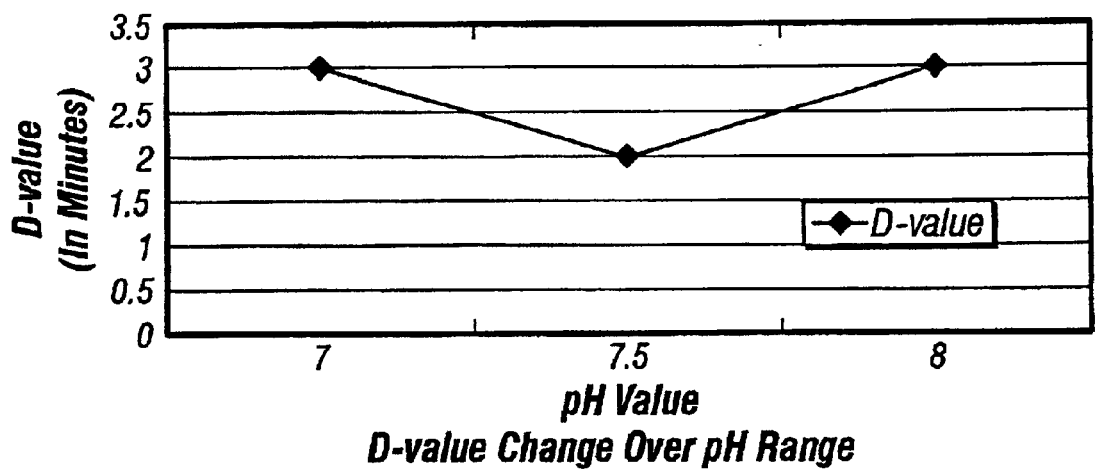
FIG. 2 shows the actual D-value changes as the pH changes over time for the composition of the Example 2.

Peroxycarboxylic acids for use as medical germicides can be prepared in-situ in aqueous solutions utilizing sodium perborate and acyl/aroyl donating compounds. In its crystalline form, sodium perborate exists as a dimeric cyclic peroxodiborate salt, $Na_2[B_2(O_2)_2(OH)_4]$. It may be configured as a powder, compressed powder, or tablet. When added to water, perborate hydrolyses to form the peroxoborate complex ion $(HO)_3BOOH^-$, and other borate species. At acidic pH, the peroxoborate anion further hydrolyses to form tetrahydroxy borate anions, $B(OH)_4^-$, and hydrogen peroxide, $H_2O_2$. At alkaline pH, however, the peroxoborate species has the ability to donate a peroxo group as a nucleophile to the carbonyl carbon of an acyl/aroyl donor: a compound with an appropriately stable leaving group alpha to the carbonyl carbon (eg. esters, imides, et al.). This results in the formation of a peracyl anion that then forms an equilibrium amount of the corresponding conjugate peracid.

This invention addresses the use of sodium perborate and novel acyl and/or aroyl donors (those other than acetyl) to generate peroxycarboxylic acids other than peracetic acid for use as germicide solutions.

The present invention takes advantage of the above chemistry to provide a specific formulation useful for both skin topical surface microbial kill and for use as a cold temperature disinfectant/sterilant. In particular, the present composition includes a sodium perborate at percentage levels of from 20% to 50%, preferably from 40% to 45%. Generally speaking, the perborate can be any Group I metal perborate but is preferably sodium perborate because of its ease of availability and economics. Specifically, Perborate is mixed with one or more acyl donors having the following general formula:

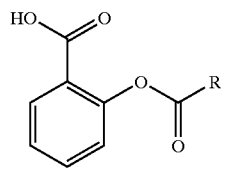

wherein R equals $C_2$–$C_{10}$alkyl, straight chain, branched chain or cyclic. Preferably R is $C_2$ or $C_3$ making the acyl donors propionyl salicylic acid or butyrylsalicylic acid. The amount of acyl donor should be from approximately 1.0% to 50% by weight of the powdered composition preferably from 40% to 45%.

The third essential ingredient is a buffering system of one or more buffers. As used herein, the term buffering system means one or more buffers that performs the following functions: Kinetically raises the pH of the solution to approximately 9 for rapid formation of the peracid; and then the pH then drops to approximately 7.5±0.5 for improved peracid stability and anti-microbial efficacy. The pH of this buffer system takes approximately 15–30 minutes to stabilize at ambient conditions. The composition of the buffering system can be adjusted to bring about desired changes in buffering capacity, ionic strength and osmolarity. The composition of the buffering system can also be adjusted to improve corrosion inhibition. Generally speaking, the buffer can be a combination of monobasic, dibasic, and/or tribasic Group I phosphates, either as hydrates or anhydrous salts. The rate of dissolution can be controlled in that phosphate hydrates typically dissolve in water faster than anhydrous phosphates. The amount of the buffer in terms of its overall weight to the powdered composition should be from 1% to 30%, preferably 5% to 15%.

A fourth ingredient, not essential but highly preferred for the composition, is a surfactant which facilitates microbial kill. Suitable surfactants can come from the list of our earlier common assignee's U.S. Pat. No. 6,096,348 which is incorporated herein by reference. Generally, those can include suitable detergents or surfactants that upon testing may reveal an enhancement of microbial kill. The amount of such surfactant can be within the range of from 0.005% by weight to about 1.0% by weight of the composition preferably from 0.01% to 0.5% by weight of the composition. Typical examples include anionics such as alkyl sulfate surfactants. Alkyl sulfate surfactants are a type of anionic surfactant of importance for use herein. Alkyl sulfates have the general formula $ROSO_3M$ wherein R preferably is a $C_{10}$–$C_{24}$ hydrocarbyl, preferably an alkyl or hydroxyalkyl having a $C_{10}$–$C_{20}$ alkyl component, more preferably A $C_{12}$–$C_{18}$ alkyl or hydroxyalkyl, and M is H or a cation, e.g., an alkali metal cation (e.g., sodium, potassium, lithium), substituted or unsubstituted ammonium cations such as methyl-, dimethyl-, and trimethyl ammonium and quaternary ammonium cations, e.g., tetramethylammonium and dimethyl piperdinium, and cations derived from alkanolamines such as ethanolamine, diethanolamine, triethanolamine, and mixtures thereof, and the like. Typically, alkyl chains of $C_{12-16}$ are preferred for lower wash temperatures (e.g., below about 50° C.) and $C_{16-18}$ alkyl chains are preferred for higher wash temperatures (e.g., above about 50° C.).

Alkyl alkoxylated sulfate surfactants are another category of useful anionic surfactant. These surfactants are water soluble salts or acids typically of the formula $RO(A)_mSO_3M$ wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydroxyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl-, trimethyl-ammonium and quaternary ammonium cations, such as tetramethyl-ammonium, dimethyl piperydinium and cations derived from alkanolamines, e.g., monoethanolamine, diethanolamine, and triethanolamine, and mixtures thereof. Exemplary surfactants are $C_{12}$–$C_{18}$ alkyl polyethoxylate (1.0) sulfate, $C_{12}$–$C_{18}$ alkyl polyethoxylate (2.25) sulfate, $C_{12}$–$C_{18}$ alkyl polyethoxylate (3.0) sulfate, and $C_{12}$–$C_{18}$ alkyl polyethoxylate (4.0) sulfate wherein M is conveniently selected from sodium and potassium.

Other anionic surfactants useful for detersive purposes can also be included in the compositions hereof. These can include salts (including, for example, sodium, potassium, ammonium, and substituted ammonium salts such as mono-, di- and triethanolamine salts) of soap, $C_9$–$C_{20}$ linear alkylbenzenesulphonates, $C_8$–$C_{22}$ primary or secondary alkanesulphonates, C8–C24 olefinsulphonates, sulphonated polycarboxylic acids, alkyl glycerol sulfonates, and fatty acyl glycerol sulfonates.

The most preferred, because it has been found to be the most universally effective, are alkylarylsulphonates and most preferably dodecylbenzenesulphonic acid salts, and most preferably the sodium salts of such acids.

The composition can also of course include other minors. By minors, Applicant means compounds which do not affect the microbial action but which have other desirable properties and may be added to tailor for a specific use including, but not limited to corrosion inhibitors such as fatty amine salts, for example, n–n', dibutylurea. Minors may also include those to make the composition more pharmaceutically elegant such as for example, odorants or dyes, etc. Generally these minors are at levels of from 0.001% by weight to about 5% by weight.

As those skilled in the art know, D-value determination provides a graphic representation of the kill kinetics of a disinfection/sterilization method. There are several methodologies to obtain the average D-value, the negative reciprocal of the slope of a (straight) line of a graph of time versus population, and is defined as the time interval required to reduce a microbial population 1 log, or 90%. Each species for a particular disinfectant/sterilant will have its own D-value. Generally, the lipid viruses and vegetative bacteria are easiest to kill (shortest D-value), with bacterial spores being the most resistant (longest D-value).

The following examples are shown to illustrate but not limit the invention.

EXAMPLE 1

| Invention Formulation: | Amount |
|---|---|
| Sodium perborate monohydrate | 5.0 g |
| Butyrylsalicylic acid | 5.4 g |
| Sodium phosphate monobasic (monohydrate) | 1.2 g |
| Dodecylbenzenesulfonic acid sodium salt | 0.00625 g |

EXAMPLE 2

| Invention Formulation: | Amount |
|---|---|
| Sodium perborate monohydrate | 5.0 g |
| Propionylsalicylic acid | 5.0 g |
| Sodium phosphate monobasic (monohydrate) | 1.2 g |
| Dodecylbenzenesulfonic acid sodium salt | 0.00625 g |

Both of the above formulations were blended, then dissolved in 500 ml of water. The pH of the solution at 1 hour was approximately 7.6.

The D-value here achieved is typically 2–3 minutes and a six log reduction of the challenge spore (*Bacillus stearothermophilus*) is consistently achieved with Example 2. Thus a D-value of approximately 3 minutes or less can be obtained. Moreover, as illustrated by the above example, indications are such that it can be used effectively for instrument disinfection or sterilization and topical microbial kill. It also demonstrates potential automated endoscope reprocessor (AER) compatibility, low toxicity and a linear kill rate.

What is claimed is:

1. The powdered composition which reacts in water to form one or more peroxycarboxylic acids in an antimicrobial effective concentration providing surface disinfection/sterilization of human and animal skin, tissue and body cavities; and medical devices/instruments, comprising:

from about 20% by weight to about 50% by weight of one or more perborates;

from about 1% by weight to 50% by weight of one or more acyl donors of the formula:

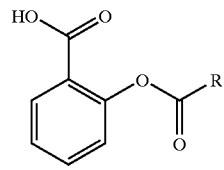

wherein R is $C_2$–$C_4$ alkyl, straight chained, branched, or cyclic, and from about 1% to 30% by weight of a buffering system which consists of a combination of monobasic, dibasic and/or tribasic sodium phosphate, either as hydrates and/or anhydrous salts; and from about 0.005% to 1.0% by weight of an alkylaryl sulfonate surfactant.

2. The composition of claim 1 which has a D-value of six minutes or less at or below 60 degrees ° C. for disinfection/sterilization of medical devices/instruments.

3. The composition of claim 2 wherein the alkylaryl sulfonate surfactant is the sodium salt of dodecylbenzenesulfonic acid.

* * * * *